United States Patent [19]

Schneider

[11] 4,043,943
[45] Aug. 23, 1977

[54] PROCESS FOR PRODUCING A MIXED OXIDE OF VANADIUM AND PHOSPHORUS HAVING AN IMPROVED INTRINSIC SURFACE AREA

[75] Inventor: Ronald A. Schneider, Berkeley, Calif.

[73] Assignee: Chevron Research Company, San Francisco, Calif.

[21] Appl. No.: 612,823

[22] Filed: Sept. 12, 1975

Related U.S. Application Data

[60] Division of Ser. No. 521,428, Nov. 6, 1974, which is a continuation of Ser. No. 274,685, July 24, 1972, abandoned, which is a continuation-in-part of Ser. No. 263,883, June 19, 1972, abandoned.

[51] Int. Cl.$^2$ .............................................. B01J 27/14
[52] U.S. Cl. .................................... 252/437; 252/435

[58] Field of Search ................ 252/437, 435; 423/305

[56] References Cited

U.S. PATENT DOCUMENTS 3,156,706  11/1964  Kerr ................................ 252/437 X
3,156,707  11/1964  Kerr .................................. 252/437

Primary Examiner—O. R. Vertiz
Assistant Examiner—Gregory A. Heller
Attorney, Agent, or Firm—D. A. Newell; John Stoner, Jr.; W. Keith Turner

[57] ABSTRACT

A solid vanadium (IV) phosphate having an improved intrinsic surface area is prepared by precipitating the solid from an essentially organic liquid medium at a temperature in the range 0° C. to 200° C.

2 Claims, No Drawings

PROCESS FOR PRODUCING A MIXED OXIDE OF VANADIUM AND PHOSPHORUS HAVING AN IMPROVED INTRINSIC SURFACE AREA

CROSS-REFERENCE TO RELATED APPLICATION

This application is a division of application Ser. No. 521,428, filed November 6, 1974, which, in turn, is a continuation of application Ser. No. 274,685, filed July 24, 1972, now abandoned which, in turn, is a continuation-in-part of U.S. application Ser. No. 263,883, filed June 19, 1972, now abandoned, U.S. Pat. No. 3,864,280 issued fred Ser. No. 298,074, which is a division application from Ser. No. 263,883.

Field of the Invention

This invention relates to a process for the production of an improved mixed oxide of vanadium and phosphorus, e.g., a vanadium (IV) phosphate, and, more particularly, to a crystalline mixed oixde of vanadium and phosphours having an intrinsic surface area in excess of about 5 square meters per gram.

Prior Art Description

Mixed oxides which comprise vanadium and phosphorus are known and used in the chemical art, especially as catalysts for the conversion of hydrocarbon feeds to useful products, for example, for the partial oxidation with molecular oxygen or with molecular oxygen and ammonia of a volatile hydrocarbon feed for the production of maleic anhydride, acrylonitrile, and the like. In the usual method of preparation, the mixed oxide is prepared by the interaction of a suitable compound of vanadium with a suitable compound of phosphorus in a reaction which is carried out in a water medium or in the absence of a liquid diluent. In the former method, the oxide is produced by evaporation of all or part of the water. In the latter, the reactants are either fused or liquid phosphoric acid is mixed with a solid vanadium oxide until reaction ensues. These composites suffer from the disadvantage in that they have been found to have intrinsic surface areas [BET Method - H. Brunauer, P. H. Emmett, E. Teller, J.A.C.S., 60, 309 (1938)] of only 2–4 square meters per gram. Such limited intrinsic surface areas are undesirable because it has also been found that the activity of these mixed oxides is, in general, directly related to the intrinsic surface area.

THE INVENTION

A process has now been found for the preparation of a vanadium (IV) phosphate which has an improved intrinsic surface area. In the process a vanadium (IV) phosphate is precipitated from a suitable liquid medium at a temperature in the range from 0° C. to 200° C., preferably 65° C. to 150° C., and at a pressure sufficient to maintain the liquid medium. A suitable medium is one which is a liquid at the precipitation temperature and which contains at least 15 volume percent of a relatively unreactive organic oxygen-containing component. In may contain a minor (less than 20 volume percent of the medium) amount of water. It may also contain up to 85 volume percent of an inert diluent.

The oxygen-containing component is one or more relatively unreactive compounds composed of:

1. carbon, hydrogen and oxygen which have a carbon atom content in the range from 1 to about 15 and an oxygen atom content in the range 1 to 4;
2. compound of (1) in which 1, 2 or 3 of the hydrogen atoms are replaced by 1, 2 or 3 atoms of chlorine, or a mixture of compounds of groups (1) and (2).

The inert diluent is one or more relatively unreactive organic compounds composed of:
   a. carbon and hydrogen;
   b. carbon, hydrogen and halogen;
   c. carbon and halogen; or
   d. a mixture of the compounds of groups a), b) and c); the foregoing diluent compounds are also characterized:
1. in that they are liquids at the precipitation temperature;
2. in that the halogen is chlorine or bromine; and
3. in that the carbon atom content of the compounds is in the range from 1 to 20.

The above description of the liquid medium has reference to the composition of the medium at the incipient precipitation stage, that is, the composition at the time the solid precipitate begins to form, and thereafter. In a preferred embodiment, the precipitation medium contains about 1 mol of water per gram atom of phosphorus during the formation of the precipitate, and this water in the main is incorporated in the solid precipitate. Also, for each gram atom of vanadium in the medium, an amount of orthophosphoric acid in the range 0.9 to 3 mols, preferably 0.9 to 2 mols, should be present.

The relative amount of the vanadium desirably present per liter of the liquid medium varies depending upon the composition of the medium and the precipitation method. In general, a satisfactory amount is in the range 0.05 to 10 gram atoms of vanadium per liter of the liquid medium.

The precipitation is effected by methods as known in the crystallization art. These include precipitation effected by one or more of the following:
1. Removal of all or part of the liquid medium by evaporation;
2. Removal of all or part of the liquid medium by distillation;
3. Cooling the medium from a higher to a lower temperture in the process temperature range;
4. Adding one or more of the suitable organic liquids to the medium with the added compounds relative to the medium being inferior solvents for the vanadium (IV) phosphate;
5. Forming in situ a supersaturated liquid medium by mixing together two separate portions of the medium in which the first portion contains as a solute a suitable vanadium (IV) or (V) compound and the other contains orthophosphoric acid.

The precipitated vanadium (IV) phosphate is separated from the liquid medium by filtration, centrifugation, settling and decantation or by evaporation of the liquid medium. It is then freed of volatile material (adsorbed or chemisorbed organic compounds and water) by calcination at a temperature in the range 100° C. to 500° C.

Surprisingly, the mixed oxides (phosphates) obtained by the process of the invention have intrinsic surface areas which greatly exceed the intrinsic surface areas of the mixed oxides or phoshates precipitated from and essentially aqueous medium. In general, the difference is substantial and is usually at least a two-fold increase and often is as much as a 10- to 15-fold increase in intrinsic surface area.

By relatively unreactive, as used herein, having reference to oxygen-containing organic compounds and to diluent compounds is meant by definition:

1. that the compound does not set (polymerize) or decompose when in contact with hydrochloric or phosphoric acids or a mixture of these acids at the temperature of use; and
2. as a practical matter, little or none of the compound reacts with hydrogen chloride or phosphoric acid or a mixture of hydrogen chloride and phosphoric acid at the temperature of use.

By intrinsic surface areas, as used herein, is meant by definition the surface area of the vanadium (IV) phosphate in the absence of a carrier, support material or extender; that is, the surface area of the composition of itself.

By a vanadium (IV) phosphate, as used herein, is meant that the mixed oxide composite has a substantial content of vanadium atoms in the plus 4 valence (oxidation) state, i.e., at least 25 percent of the vanadium component is of the plus 4 state.

EMBODIMENT

In a preferred embodiment of the invention vanadium (IV) phosphate is formed in situ in a reaction carried out in a dry acetic acid mediium using vanadium pentoxide, hydroen chloride, orthophosphoric (100%) acid and paraformaldehyde. The acetic acid and reagents are charged to a glass or corrosion resistant vessel fitted with a stirring means, a reflux condenser, and a condensate take-off head. The reactor is also fitted for the introduction of a gas into a basal portion of the body of acetic acid. For each liter of acetic acid 1 formula ($V_2O_5$) weight of vanadium pentoxide, 2.4 mols of the phosphoric acid and 1.0 mol of formadlehyde in paraformaldehyde form are charged to the reactor. The reactor and charge are then heated with stirring to the reflux temperature. Thereafter, while maintaining the reflux temperature, a stream of anhydrous hydrogen chloride gas is introduced into the acetic acid-reactants mixture. Dissolution of the solid vanadium pentoxide is rapid and is moderately exothermic. When the dissolution of the vandium pentoxide is completed, the introduction of the hydrogen chloride is stopped. The refluxing, however, is continued until the vanadium component in the solution has an average valence in the range 3.9–4.3 or the solution has changed to a brownish-green color.

Next the solution is concentrated by removal of acetic acid by distillation. The dissolved hydrogen chloride is also expelled from the acetic acid solution and vented. To facilitate removal of the hydrogen chloride, a stream of nitrogen gas is introduced into the acetic acid solution and used as a sparging means. The stream of nitrogen also reduces the tendency of the solution to bump during the distillation as solid vanadium (IV) phsophate precipitates from the concentrating solution. After the hydrogen chloride in large part has been vented and one-third of the acetic acid charge has been distilled overhead, the distillation is discontinued and the still bottom cooled to the ambient temperature. The residue is a mixture of a green crystalline precipitate and a clear colorless supernatant liquid, acetic acid. The green solid is conveniently separated from the liquid by filtration. The collected solid is then freed of volatiles, mainly acetic acid, by drying to constant weight in a vented drying oven maintained at 150° C. The dried solid is a free-flowing, emerald-green powder which has an intrinsic surface area before activation of about 10 square meters per gram, and after activation of about 15 to 25 square meters per gram. For use as a catalyst in a fixed bed vapor phase oxidation of n-butane, the dried green powder is mixed with stearic acid (3 weight percent based upon the green solid), tabletted, crushed to 20/28 mesh (Tyler Standard), and activated by heating. For the production of maleic anhydride from n-butane, the activity (399° C.) and selectivity (102 weight percent) of the activated catalyst is excellent.

PRECIPITATION MEDIA

Organic compounds which contain oxygen, which are liquids and which are relatively unreactive at the temperature of the employment as media, are satisfactory for use in the process. An oxygen content of a single oxygen atom per molecule is sufficient for the required effect. Usually the oxygen content will be in the range 1 to 4 atoms per molecule and the balance of the compound will be carbon and hydrogen. For reasons of cost, convenience in handling and the like, ordinary oxygen-containing compounds such as alcohols, carboxylic acids, ethers, hydroxyethers, amides, and the like are especially satisfactory media.

The carbon atom content of the oxygen-containing compound may vary widely. A content in the range 1 to 15 carbon atoms per molecule includes, in general, the more satisfactory of these compounds useful as media for my process. The range 1 to 10 is preferred.

Relatively unreactive derivatives of the above-described compounds are also satisfactory for use as media for may process. As many as three, but usually only one, hydrogen atom of the parent compound may be replaced by inert substituent such as chloride or bromide.

The organic media described above may be diluted with a relatively unreactive diluent. Suitable diluents should be in the liquid phase at the temperature of use, and should have a carbon atom content in the range 1 to 20. These include hydrocarbons, mono- and poly-chlorinated hydrocarbons, and the like diluents.

For a useful effect in the increasing of the intrinsic surface area of the precipitated vanadium (IV) phosphate, the organic liquid medium for the precipitation must contain an appreciable amount of an oxygen-containing compound. The effective amount varies depending upon the particular compound(s) employed. In general, a volume percent of at least 15 percent will be satisfactory. Preferably, the entire liquid medium is an oxygen-containing compound of a mixture of oxygen-containing compounds.

For reasons of cost and availability, oxygen-containing organic compounds preferred for use in the process include the following classes:

1. Primary and secondary alcohols of the formula ROH, in which R is a saturated hydrocarbon group or a phenylalkyl group;
2. Ethers of the fomrula ROR, in which R is a saturated hydrocarbon group which contains at least 2 carbon atoms;
3. Ether-acids of the formula ROR'$CO_2$H, in which R and R' are saturated hydrocarbon groups;
4. Ether-alcohols of the fomrula ROR'OH, in which R and R' are primary or secondary saturated hydrocarbon groups; and 5-and 6-membered ring cyclic ethers of the formula

in which R is a bivalent saturated hydrocarbon group.

Representative organic compounds useful as a liquid medium and as components of a suitable liquid medium herein include methanol, ethanol, 1-propanol, 2-propanol, 1-butanol, 2-butanol, 2-methyl-1-propanol, 3-methyl-2-butanol, 1-pentanol, 2-pentanol, 3-pentanol, 2-methyl-1-butanol, 3-methyl-1-butanol, 2,2-dimethyl-1-propanol, 1-hexanol, 4-methyl-1-pentanol, 1-heptanol, 4-methyl-1-hexanol, 3-ethyl-1-pentanol, 1-octanol, 2-ethyl-1-hexanol, 4-methyl-1-heptanol, 2-propyl-1-pentanol, 1-dodecanol, 4-propyl-1-nonanol, 1-tetradecanol, 4,5-dimethyl-1-decanol, 2,4-trimethyl-1-pentanol, 2,4,6,8-tetramethyl-1-decanol, 1,2-ethanediol, 1,2-propanediol, 1,4-butanediol, 1,8-octanediol, 1,2-tetradecanediol, glycerol, trimethylol propane, diethylene glycol, cyclohexanol, 2-methoxy-1-ethanol, 2-ethoxy-1-ethanol, 4-methoxy-1-butanol, triethylene glycol; acetic, propionic, butyric, glycollic, pentanoic, hexanoic, methoxyacetic, ethoxyacetic, butoxyacetic acids; diethyl ether, dipropyl ether, dibutyl ether, tetrahydrofuran, 1,4-dioxane, tetrahydropyran, 1,4-dimethoxy butane, 1,4-diethoxy butane, dimethoxy ethane; methyl acetate, ethyl acetate, propyl acetate, butyl acetate, pentyl acetate, hexyl propionate, methyl propionate, ethyl propionate, n-butyl propionate, 2-ethyl-1-hexyl acetate, dimethyl succinate, diethyl succinate, diethyl adipate, 2-methoxy-1-ethyl acetate, ethyl methoxy acetate, methyl tetrahydrofuroate, methyl benzoate; others include citronellol, 3-phenyl-1-propanol, 2-cyclohexyl-1-ethanol, tetrahydrofurfuryl alcohol, 2-acetoxy-1-ethanol, methyl lactate, 4-methyl-3-penten-1-ol, phenol, p-cresol, thylmol, phenylacetic acid, 4-methyl-3-pentenoic acid, hexahydrobenzoic acid, anisol; acetone, methyl ethyl ketone, methyl isobutyl ketone, cyclohexanone, cyclopentanol, xylenols, benzyl alcohol; inertly substituted oxygen-containing compounds such as 2-chloro-1-ethanol, 3-bromo-1-propanol, 2,2-di(-chloromethyl)-1-ethanol, 3,4-dibromo-1-hexanol, 2,2,2-trichloroethanol, 2-chloro-3-bromo-1-heptanol, 4-chloro-2-ethyl-1-hexanol, 2,4,6-trichloro-1-decanol; chloroacetic, dichloroacetic and trichloroacetic acids, 2-chloropropionic, 2,2-dichloropropionic, 2,2,3-trichloropropionic acids; bromoacetic, 4-bromohexanoic, 4,6-dibromooctanoic, 3-chloro-4-bromopentanoic acids; 3-chlorotetrahydrofuran, 3-bromotetrahydrofuran, 2,2'-dibromoethyl ether, 3,3'-dichlorodipropyl ether, 3,4-dichlorotetrahydrofuran, 3-bromotetrahydropyran; methyl chloroacetate, ethyl chloroacetate, propyl chloroacetate, 2-chloroethyl chloroacetate, 2-bromopropyl dichloroacetate, pentyl trichloroacetate, butyl bromoacetate, and the like oxygen-containing and inertly substituted oxygen-containing compounds.

Representative inert diluent compounds include hexane, heptane, octane, cyclohexane, methylcyclopentane, 2,2,4-trimethylpentane, dodecane, 2-ethylhexane, 3-octene, cyclohexene; benzene, toluene, o-xylene, m-xylene, p-xylene, ethylbenzene, trimethylbenzene, 2-propylbenzene; methylene chloride, chloroform, carbon tetrabromide, carbon tetrachloride 3-chlorohexane, 2,3-dichlorooctane, chlorocyclohexane, 1,2-dichloropentane, 1,2-dichloroheptane, 1,1,2-trichloroethane; chlorobenzene, bromobenzene, o-dichlorobenzene, p-dichlorobenzene, 2-chlorotoluene, 4-chlorotoluene, 2,4-dichlorotoluene, 1,3-dimethyl-4-chlorobenzene, butyl bromide, and the like hydrocarbons and halogenated hydrocarbons.

Water

Only a relatively minor amount of water may be present at most in the precipitation medium *at the time of the precipitation*. Water, when present in excess at this time, exerts a leveling effect upon the intrinsic surface area of the precipitating vanadium (IV) phosphate. What constitutes a permissible amount of water which may be present varies depending upon the particular organic medium and oxygen-containing compound(s) being used. In general, a satisfactory or tolerable amount of water will be in the range where the water constitutes from about 0 to about 20 volume percent of the liquid mixture. Preferably, based upon the phosphorus in the liquid medium, an amount of water in the range 0 to 2 mols per gram atom of phosphorus is present in the liquid medium. If present, and depending upon the medium, excess water may be conveniently removed by distillation, azeotropically or otherwise, by ordinary means such as the use of a suitable drying agent, or by a suitable chemical reaction, for example by the addition of acetyl chloride, acetic anhydride or the like reactive hydrolysable compounds to the organic medium prior to precipitation of the vanadium (IV) phosphate.

The Precipitation

Precipitation methods, in general, may be used to effect the deposition of the vanadium (IV) phosphate from the organic medium and these methods are contemplated for use herein. These, in general, are the techniques employed in conventional crystallizations in the chemical art and include removal of the solvent be evaporation, or distillation, cooling of the medium, selective removal by distillation of a good solvent component from a medium composed of a mixture of good and poor solvent components, addition of a poor solvent to the liquid medium, creating a supersaturated liquid medium by mixing two solutions each containing different reactants, a combination of these operations, and the like. In one preferred mode, the liquid medium is separated from the vanadium (IV) phosphate by evaporation to substantial dryness, that is, until little or no change in weight of the precipitate occurs upon continued heating. For the separation of solid-liquid slurries, ordinary means, such as filtration, centrifugation, and the like ae satisfactory.

Vanadium (IV) phosphates are polar materials. Thus, where it is desired to precipitate a high surface phosphate of the invention from a solution after only a partial removal of the liquid or with no removal of the liquid medium, it is often advantageous to reduce the polarity of the medium by adding a relatively nonpolar inert organic diluent such as a hydrocarbon or a chlorinated hydrocarbon to the organic medium containing the vanadium (IV) phosphate. Representative diluents include benzene, toluene, xylene mixtures, alkane solvent cuts (i.e., $C_5$-$C_{10}$ single and mixed alkane compounds), the $C_1$-$C_{10}$ chlorinated alkane hydrocarbons, and the like.

The usual considerations, as known in the crystallization art, apply relative to what desirably is the concentration of the vanadium (IV) phosphate in the liquid medium. Usually, an excess of the medium is employed for convenient handling, and depending upon the procedure of choice, all or part of the liquid medium is evaporated. In general, the medium will contain from 1 to 50 weight percent of the vanadium (IV) phosphate prior to the precipitation.

Depending upon the precipitation procedure, a satisfactory temperature will be in the range from 0° C. to 200° C., preferably 65° C. to 150° C. in the case where precipitation is effected by evaporation of the liquid medium to dryness is used. In the case where no liquid is evaporated or only a partial removal of the liquid medium is effected, a temperature in the range from 0° C. to 150° C. is peferred. The use of a temperature about 150° C. is usually less convenient.

Vanadium (IV) Phosphate

Vanadium (IV) phosphate salts are conveniently prepared in situ in the precipitation medium. Vanadium (V) oxysalts, vanadium (V) oxide ($V_2O_5$) and ammonium metavanadate ($NH_4VO_3$) are the forms in which vanadium compounds are usually available commercially. It is known in the art that vanadium in the plus 5 valence or oxidation state can be readily reduced to the plus 4 state and these methods are, in general, satisfactory in the organic media for use in the present process (see, for example, "*Oxidations of Organic Compounds With Quinquivalent Vanadium,*" by J. S. Littler and W. A. Waters, J.C.S., 1959, Pages 1299–1305). Frequently, the organic medium or a portion of it serves as a reducing agent and as a medium where a vanadium (V) compound is used for an in situ preparation of a vanadium (IV) phosphate. The oxidation or reduction of vanadium in the range plus 3 to plus 5 is well known in the art and is not of itself a feature of the instant invention. Vanadium (IV) oxide and vanadium (IV) oxysalts of relatively volatile (B.P. below 213° C. at 1 atm pressure) inorganic acids or of organic ($C_1$-$C_{25}$-carbon atom content) carboxylic acids, in general, and the like are also satisfactory for use herein and are contemplated for use.

The vanadium (IV) and (V) oxychloride and bromide salts are soluble in the oxygenated organic media herein, as is the case also for orthophosphoric acid. Therefore, a convenient in situ preparation includes the solubilization of an insoluble vanadium compound by interaction of the compound as a dispersed solid in the organic medium with hydrogen chloride or hydrogen bromide. Also, in cases where dissolution of the vanadium compound is slow, or a nonphosphate precipitate forms as an intermediate, the application of a hydrogen halide acid is, in general, a useful means for accelerating the formation of the desired solution. After adjusting the average valence of the dissolved vanadium when necessary to bring it into the range plus 3.8 to 4.6, a pentavalent phosphorus acid, e.g., orthophosphoric acid or a suitable precursor of this acid is added to the medium for the in situ preparation of the vanadium (IV) phosphate. Representative combinations of reactants are illustrated by the following illustrative and simplified reaction summarizing equations:

(1) $VOCl_3 + H_3PO_4 + XH_2O + \text{Reducing Agent} \xrightarrow{(HCl)}$
Vanadium (IV) phosphate and volatile by-products (2) $V_2O_5 + 2 POCl_3 + XH_2O + \text{Reducing Agent} \xrightarrow{(HCl)}$
Vanadium (IV) phosphate and volatile by-products (3) $NH_4VO_3 + POCl_3 + XH_2O + \text{Reducing Agent} \xrightarrow{(HCl)}$
Vanadium (IV) phosphate and volatile by-products (4) $V_2O_5 + PCl_3 + H_3PO_4 + 4.2H_2O \xrightarrow{(HCl)}$
Vanadium (IV) phosphate and volatile by-products (5) $V_2O_5 + 2 H_3PO_4 + 1 C_6H_5CHO \xrightarrow{(HCl)}$
Vanadium (IV) phosphate and volatile by-products (6) $V_2O_3 + V_2O_5 + 4 H_3PO_4 \xrightarrow{(HBr)}$
Vanadium (IV) phosphate and volatile by-products (7) $V_2O_5 + 3 N_2O_3 + 2 H_3PO_4 \xrightarrow{(HCl)}$
Vanadium (IV) phosphate and volatile by-products (8) $2 VOBr_3 + 9 H_2O + P_2O_5 + \text{Reducing Agent} \xrightarrow{(HBr)}$
Vanadium (IV) phosphate and volatile by-products (9) $VOI_2 + HPO_3 + 2 H_2O \xrightarrow{(HI)}$
Vanadium (IV) phosphate and volatile by-products

(10) $V_2O_5 + H_4P_2O_7 + 2 H_2O + \text{Reducing Agent} \xrightarrow{(HCl)}$
Vanadium (IV) phosphate and volatile by-products

(11) $2 VOCl_3 + H_3PO_4 + HPO_2 + 6 H_2O \xrightarrow{(HCl)}$
Vanadium (IV) phosphate and volatile by-products

(12) $VO(CH_3CO_2)_2 + H_3PO_4 + H_2O \xrightarrow{(HCl)}$
Vanadium (IV) phosphate and volatile by-products

(13) $VCl_4 + H_3PO_4 + 2 H_2O \longrightarrow$
Vanadium (IV) phosphate and volatile by-products In summary, one embodiment of this invention for the production of a solid vanadium (IV) phosphate having an intrinsic surface are of at least 10 square meters per gram, comprises:

I. Dissolving a vanadium-containing feed in a liquid medium at a temperature in the range from about 0° C. to 200° C. and a pressure sufficient to maintain the liquid medium in the presence of an anhydrous gas selected from the group consisting of hydrogen chloride and hydrogen bromide, said medium consisting essentially of one or more relatively unreactive compounds selected from the group consisting of:
1. Compounds composed of carbon, hydrogen and oxygen, said compounds having a carbon atom content in the range from 1 to about 15 and an oxygen atom content in the range 1 to 4;
2. Compounds of Group (I) wherein from 1 to 3 of said hydrogen atoms are replaced by from 1 to 3 atoms of chlorine;
3. Compounds composed of carbon and hydrogen, of carbon, hydrogen and halogen, or of carbon and halogen; said compounds having a carbon atom content in the range from 1 to 20 and said halogen being selected from the group consisting of chlorine and bromine; and
4. Water;

said medium containing:
a. at least 15 volume percent of said oxygen-containing organic compounds;
b. an amount of water in the range from 0 to about 20 volume percent of the medium; and
c. an amount of vanadium in the range from about 0.05 to 10 gram atoms per liter of the medium;

said vanadium-containing feed consisting essentially of one or more compounds selected from the group consisting of vanadium (IV) or (V) oxides, ammonium metavanadate, and a vanadium (IV) or (V)

oxysalt of a relatively volatile inorganic acid or of an organic carboxylic acid;

II. Adjusting the average valence of the vanadium content of said feed to a value in the range from about plus 3.8 to 4.6 by:
  1. Maintaining the resulting solution at a temperature in said range for a period in the range from about 1 to 10 hours and sufficient to effect said adjustment; or
  2. Adding at least a stoichiometric amount of a suitable reducing or oxidizing agent to the resulting solution and maintaining the temperature as in (1);

III. Forming a vanadium (IV) phosphate by adding an amount of a pentavalent phosphorus acid to the solution containing the valence adjusted vanadium, said amount being in the range from about 0.9 to 3 mols per gram atom of vanadium present in the solution; and IV. Precipitating said vanadium (IV) phosphate from the solution by one or more of the following procedures:
  1. Removing all or part of the liquid medium by evaporation;
  2. Removing all or part of the liquid medium by distillation;
  3. Cooling the medium from a higher to a lower temperature in the process temperature range; and
  4. Adding one or more of the suitable organic liquids to the medium with the added compounds relative to the medium being inferior solvents for the vanadium (IV) phosphate.

Alternatively, steps may be combined. For example, the vanadium (IV) phosphate solution is prepared by combining the vanadium-containing feed, the pentavalent phosphorus acid and liquid medium in a reaction vessel in the presence of the hydrogen halide gas at a temperature in the range from about 0° C. to 200° C. Following the vanadium (IV) phosphate solution preparation the precipitation of the vanadium (IV) phosphate is effected by the aforementioned procedures.

By varying the relative amounts of the vanadium- and phosphorus-containing reactants, a range of atomic ratios of the phosphorus to vanadium in the precipitated vanadium (IV) phosphate is obtained. Excellent results in terms of intrinsic surface area enhancement appear to result in the present method when the phosphorus to vanadium atomic ratio is in the range 0.9–2.0 to 1, especially 1.0–1.3 to 1.

The average valence (oxidation state) of the vanadium desired in the finished catalyst varies depending upon the particular hydrocarbon conversion involved. In general, the average valence of the vanadium component of useful phosphates will be in the range plus 3.8 to plus 4.6 and thus a substantial fraction of the vanadium present in the composite will be of the plus 4 moiety. The average valence of the vanadium can be varied somewhat by oxidative treatment or reductive treatment, as known in the art, after precipitation, as by subjecting the precipitated solid to an oxidizing or reducing atmosphere. Usually the adjustment of the average valence is more conveniently effected during or prior to the precipitation, as discussed above, by the addition of a suitable oxidizing or reducing reagent to the liquid medium and by maintaining the temperature for a period in the range from 1 to 10 hours and sufficient to effect the desired reduction or oxidation, as noted below. Thus, in equations 1, 2, 3, 5, 8 and 10, above, benzaldehyde, benzyl alcohol, or paraformaldehyde are suitable agents for the reduction. Other suitable reducing agents are known in the art and include such compounds as oxalic acid, alcohols, ketones, glycols, sugars and the like.

Where the average oxidation state of the vanadium in the medium is desirably increased, molecular oxygen, hydrogen peroxide, organic peroxides, chlorates, nitric acid and the like or electrochemical means, as known in the art, are useful for this purpose.

The examples further illustrate the invention.

In Examples 1–18, Table I, a representative variety of organic solvent media and a minor amount of water was used in the manner indicated for the preparation of solid vanadium (IV) phosphate compositions. Except where noted, these solids were at least partly crystalline. Except in Example 11, the hydrogen chloride was introduced as the anhydrous gas into the mixture of reactants and medium. The intrinsic surface areas were determined after activation and use of the composite as an oxidation catalyst (see discussion below). The gram-atomic ratio of phosphorus to vanadium was 1.2.

TABLE I

| Ex. No. | Reactants | Method | Water Added Mol/Mol Phosphorus | Solvent[1] | Intrinsic Surface Area (BET) $m^2/g$ | Oxidation State of Vanadium Used | Oxidation State of Vanadium Fresh | Remarks | Cross Reference Omit On Final |
|---|---|---|---|---|---|---|---|---|---|
| 1 | $V_2O_5$, HCl, $H_3PO_4$ | E.D.[2] | — | Water | 2–4 | 4.1 | — | Prior art method | S-118 |
| 2 | $VOCl_3$, $H_3PO_4$ | " | 1 | Tetrahydrofuran (THF) | 19 | 4.1 | 3.9 | | S-132 |
| 3 | $V_2O_5$, $POCl_3$ | " | 3 | Tetrahydrofuran (THF) | 14–21 | 4.1–4.3 | 4.0 | | S-137 |
| 4 | $VOCl_3$, $H_3PO_4$ | " | None | Tetrahydrofuran (THF) | 22 | 4.1 | | | S-138 |
| 5 | $V_2O_5$, $POCl_3$ | " | 3 | 1,2-Dimethoxyethane | 12 | 4.4 | 4.1 | | S-140 |
| 6 | $V_2O_5$, $POCl_3$ | " | 3 | 1,2-Dimethoxyethane | 15 | — | — | 33 g maleic acid added for each 100 g $V_2O_5$ | S-140MA |
| 7 | $V_2O_5$, $POCl_3$ | " | 3 | 1,2-Dimethoxyethane | 21 | 4.1 | 3.9 | 66g $(CH_3OCH_2CH_2)O$ added for each 100 g $V_2O_5$ | S-140DG |
| 8 | $V_2O_5$, $H_3PO_4$, HCl | " | None | Methanol | 8 | 4.3 | — | | S-145 |
| 9 | $V_2O_5$, $H_3PO_4$, HCl, RA[4] | " | None | Acetic acid | 10 | — | — | 2 Mol paraformaldehyde added for each mol $V_2O_5$ | S-147 |
| 10 | $NH_4VO_3$, $POCl_3$ | " | 3 | 1,2-Dimethoxyethane | 11 | — | — | | S-148 |
| 11 | $V_2O_5$, $H_3PO_4$ | " | — | Acetic acid: 37% aq. HCl::4:1 | 11 | — | — | 1 Mol benzaldehyde added for each mol $V_2O_5$ | S-151 |
| 12 | $V_2O_5$, $PCl_3$, $H_3PO_4$, HCl | P&F[3] | 1.7 | Acetic acid | 15 | 4.2 | 4.0 | | S-153 |
| 13 | $V_2O_3$, $V_2O_5$, | E.D. | None | $ClCH_2CH_2Cl:CH_3OH$ | 10 | — | — | | S-155 |

TABLE I-continued

| Ex. No. | Reactants | Method | Water Added Mol/Mol Phosphorus | Solvent[1] | Intrinsic Surface Area (BET) m²/g. | Oxidation State of Vanadium Used | Oxidation State of Vanadium Fresh | Remarks | Cross Reference Omit On Final |
|---|---|---|---|---|---|---|---|---|---|
| 14 | $H_3PO_4$, HCl $H_3PO_4$, HCl | E.D. | None | 2:1 Acetic anhydride | 5 | 4.6 | — | | S-156 |
| 15 | $V_2O_5$, $POCl_3$ | E.D. | 3 | Ethyl acetate (EA) | 6 | — | 3.9 | Amorphous | S-167 |
| 16 | $V_2O_5$, $H_3PO_4$ | E.D. | 1 | Phenol | 16 | 4.2 | — | | S-174 |
| 17 | $V_2O_5$, $H_3PO_4$ | P&F | — | $H_2O$:THF:EA 5:3:5 | 7 | | | $N_2O_3$ added | S-177 |
| 18 | $V_2O_5$, $H_3PO_4$, HCl | E.D. | None | Isobutanol | 23 | 4.2 | | | S-150 |
| 19 | $V_2O_5$, $POCl_3$ | E.D. | 3 | Acetone | 15 | 4.6 | 3.1 | | S-149 |
| 20 | $VO(CH_3CO_2)_2$, $H_3PO_4$ | E.D. | 8 | Isopropanol | 10 | — | 3.5 | | S-170 |
| 21 | $V_2O_5$, $H_3PO_4$, HCl | E.D. | None | Ethylene glycol | 19 | — | 3.6 | | S-186 |

[1]500 mls of solvent per gram atomic weight of phosphorus used. Solvent ratios are by volume.
[2]E.D. = Evaporated to dryness.
[3]P&F = Precipitated and filtered free of solvent and dried.
[4]Paraformaldehyde added as reducing agent (RA).

The above examples demonstrate that vanadium (IV) phosphates which have been precipitated from an organic medium and calcined have substantially improved intrinsic surface areas relative to the intrinsic surface areas of otherwise corresponding vanadium (IV) phosphates precipitated from an essentially aqueous medium. Other factors demonstrated by these examples include:

1. Organic ethers or hydroxylic organic solvents are, in general, superior liquid media for the preparation of vanadium (IV) phosphates having improved intrinsic surface areas;
2. The presence of an inert, oxygen-free diluent does not interfere with the preparation of vanadium (IV) phosphates and may be beneficial (compare Examples 8 and 13);
3. Organic media which tend to deplete water from the media as by hydrolysis of an acid anhydride or of an ester, in general, appear to inhibit somewhat the formation of precipitated vanadium (IV) phosphate having a greatly improved intrinsic surface area (compare Examples 14 and 15 with 9, 11, 12 and 17); and
4. Organic substances, such as maleic acid and $(CH_3OCH_2CH_2)_2O$, diglyme, tend to further improve the intrinsic surface area of a precipitated vanadium (IV) phosphate.

The high surface vanadium (IV) phosphates of the instant process are especially suitable for use as catalysts for the partial oxidation of hydrocarbon feeds by molecular oxygen. Depending upon the type reactor used, i.e., fixed bed or fluid bed, the precipitated solid is comminuted and sized by screening or slurried and extruded in the usual methods known in the art. The preparations of Table I after drying at 150° C. overnight were tested by crushing and sizing to 20/28 mesh (Tyler Standard). The sized vanadium (IV) phosphates were then charged to a fixed bed oxidizer and heated to 380° C. at a moderate rate in a flowing stream of air which passed through the bed at 1.5 volume per volume per minute. After 2 hours at temperature and this air flow rate, the air stream was replaced by an n-butane-air (1.5 volume percent n-butane) stream flowing at the 1.5 V/V/min. rate and the temperature was again increased at a moderate rate to 480° C. This condition was maintained for 10–70 hours. The temperature was then lowered to 420° C. The space velocity (VHSV) was increased to 1000 hr⁻¹ (17 V/V/min. at S.T.P.) and the temperature in most cases was adjusted until the conversion of the n-butane was 90 percent.

In Examples 22 to 42 to Table II is a list of the comparative performance data for the representative vanadium (IV) phosphates of Table I.

TABLE II

| EX. NO. | SOURCE OF CATALYST EX. NO. | INTRINSIC SURFACE AREA (BET) m²/g. | CONV. % | TEMP., ° C. | MALEIC ANHYDRIDE YIELD BASED ON BUTANE FED, WT. % |
|---|---|---|---|---|---|
| 22 | 1 | 2–3 | 90 | 485 | 77 |
| 23 | 2 | 19 | 90 | 434 | 103 |
| 24 | 3 | 14–21 | 90 | 403–412 | 93–101 |
| 25 | 4 | 22 | 90 | 420 | 96 |
| 26 | 5 | 12 | 90 | 452 | 97 |
| 27 | 6 | 15 | 90 | 422 | 89 |
| 28 | 7 | 21 | 90 | 404 | 93 |
| 29 | 8 | 8 | 90 | 468 | 90 |
| 30 | 9 | 10 | 90 | 465 | 76 |
| 31 | 10 | 11 | 90 | 472 | 73 |
| 32 | 11 | 11 | 90 | 424 | 83 |
| 33 | 12 | 15 | 90 | 399 | 92 |
| 34 | 13 | 10 | 90 | 446 | 76 |
| 35 | 14 | 5 | 16 | 510 | nil |
| 36 | 15 | 6 | 9 | 510 | nil |
| 37 | 16 | 16 | 70 | 510 | 51 |
| 38 | 17 | 7 | 91 | 491 | 58 |
| 39 | 18 | 23 | 90 | 365–382 | 105 |
| 40 | 19 | 15 | 90 | 553 | 25 |
| 41 | 20 | 10 | 4 | 510 | nil |
| 42 | 21 | 19 | 37 | 550 | nil |

The above examples demonstrate that the novel vanadium (IV) phosphates obtained by the method of the invention herein are, in general, effective and improved catalysts for partial oxidations of hydrocarbon feeds. Useful results have also been obtained in similar oxidations using butene, butadiene, benzene n-pentane, isopentane, methylcyclopentane and o-xylene feeds for the production of maleic or phthalic anhydride. Useful results have also been indicated for acrolein production and also for the case where ammonia is added to the hydrocarbon feed, as for acrylonitrile production and the like vandium (IV) phosphate catalysed hydrocarbon conversions.

PHOSPHORUS TO VANADIUM (P/V) RATIO

In the manner described in Example 18, Table I, a series of vanadium (IV) phosphate compositions were prepared, except that the relative amount of orthophosporic acid to vanadium was varied. The phosphorus to vanadium (P/V) ratios employed and the characteristics of the resulting vanadium (IV) phosphates are listed in Table II below:

TABLE III

| EX. NO. | P/V RATIO (G. atom) REACTANTS | P/V RATIO (G. atom) PRECIPITATE[(1)] | SURFACE AREA (USED CAT.,BET) $m^2/g$ | VANADIUM OXIDATION STATE USED | VANADIUM OXIDATION STATE FRESH |
|---|---|---|---|---|---|
| 43 | 0.9 | 0.9 | — | 4.9 | 4.0 |
| 44 | 1.0 | 1.0 | — | 4.5 | 4.0 |
| 45 | 1.1 | 1.1 | 27 | 4.1 | 4.0 |
| 46 | 1.2 | 1.2 | 16 | 4.3 | 3.9 |
| 47 | 1.3 | — | 20 | 4.2 | — |
| 48 | 1.5 | 1.5 | 12 | 4.0 | 3.9 |
| 49 | 1.8 | 1.7 | — | 3.9 | 3.9 |
| 50 | | | | | |

[(1)]As determined by the neutron activation method.

The above Examples 43 to 50 illustrate that the phosphorus to vanadium gram atom ratio may be varied over a range in the present method. The resulting vanadium (IV) phosphates have a substantially improved intrinsic surface area.

PROMOTERS

Minor amounts of metals in the form of oxides or phosphates are often included in vanadium (IV) phosphate catalysts as promoters. The inclusion of a minor amount (in the range from 1 to 15 gram atom percent based upon vanadium) of a Group IVB, another Group VB, a Group VIB or a Group VA metal phosphate (Periodic Chart of the Elements, F. S. Co.) in a precipitated vanadium (IV) phosphate, as herein, does not in general interfere with the formation of a phosphate having a high intrinsic surface area. Representative examples of vanadium (IV) catalysts containing a promoter were prepared using isobutanol as the organic medium and reducing agent, vanadium pentoxide, hydrogen chloride gas and 100% orthophosphoric acid. The solid phosphate was precipitated by evaporation of the organic medium followed by calcination to dryness. The representative metals and the compounds used to add them to the organic medium together with the intrinsic surface area of the resulting vanadium (IV) phosphate are listed in Table IV below.

TABLE IV

| EX. NO. | COMPOUND ADDED | AMOUNT,[(1)] G A % | SURFACE AREA $m^2/g$ (BET) |
|---|---|---|---|
| 51 | $Nb_2O_5$ | 10 | 42 |
| 52 | $Sb_2O_3$ | 10 | 27 |
| 53 | $H_2WO_4$ | 5 | 14 |
| 54 | $TiCl_4$ | 5 | 23 |

[(1)]Gram atom percent based upon vanadium.

The Examples 51–54 demonstrate that a minor amount of a promoter metal oxide may be effectively incorporated into a vanadium (IV) phosphate and yet obtain a phosphate having a high intrinsic surface area. In general, suitable compounds for the addition of the promoter metal component to the organic medium are compounds analogous to those which are satisfactory for the addition of the vanadium component in the in situ preparation of a vanadium (IV) phosphate, as described above, i.e.; the oxides, oxy-salts, halides, and the like compounds.

As the range of embodiments of this invention is wide, and many may appear to be widely different, yet not depart from the spirit and scope thereof, it is to be understood that this invention is not limited to the specific embodiments thereof, except as defined in the appended claims.

I claim:

1. A process for preparing a catalyst for catalayzing maleic anhydride production by oxidation of a hydrocarbon and which has an intrinsic surface area in excess of 5 m²/g, which preparation process comprises:
    a. forming a solution containing a vanadium compound and a phosphorus compound in an organic liquid medium, the medium containing less than 20 volume percent water and at least 15 volume percent oxygen-containing organic compounds selected from the group consisting of alcohols, carboxylic acids, ethers, esters, amides, and ketones, said medium and said vanadium and phosphorus compounds being effective so as to form a vanadium phosphate compound wherein the average valence of vanadium is between +3.8 and +4.6;
    b. precipitating said vanadium phosphate compound in said solution;
    c. removing liquid medium from the solution to obtain said vanadium phosphate compound; and
    d. calcining the vanadium phosphate compound to obtain said catalyst having an intrinsic surface area in excess of 5 m²/g.—

2. A process in accordance with claim 1 wherein the intrinsic surface area is at least 10 M²/g.

* * * * *